US006087343A

United States Patent [19]

Phillips et al.

[11] Patent Number: 6,087,343

[45] Date of Patent: Jul. 11, 2000

[54] ANTISENSE OLIGONUCLEOTIDES TARGETED TO β-1 ADRENOCEPTOR AND METHODS OF USE

[75] Inventors: Ian M. Phillips; Yuan Zhang, both of Gainesville, Fla.

[73] Assignee: University of Florida, Gainesville, Fla.

[21] Appl. No.: 09/152,717

[22] Filed: Sep. 14, 1998

[51] Int. Cl.[7] .......................... C07H 21/04; A61K 48/00; C12Q 1/68

[52] U.S. Cl. ................. 514/44; 435/6; 435/455; 435/375; 536/23.1; 536/24.1; 536/24.5

[58] Field of Search ................. 435/6, 455, 375; 536/24.1, 24.5, 23.1; 514/44

[56] References Cited

FOREIGN PATENT DOCUMENTS

WO 99/11778  3/1999  WIPO.

OTHER PUBLICATIONS

Agrawal, S., "Antisense Oligonucleotides: Towards Clinical Trials" TIBTECH vol. 14:376–387, Oct. 1996.

Branch, A., "A Good Antisense Molecule is Hard to Find" TIBS vol. 23:45–50, Feb. 1998.

Adams, S.P. et al. (1983) Hindered Dialkylamino Nucleoside Phosphite Reagents in the Synthesis of Two DNA 51–Mers. J. Am. Chem. Soc. 105: 661–663.

Agarwal, K.L., F. Riftina (1979) Synthesis and enzymatic properties of deoxyribooligonucleotides containing methyl and phenylphosphonate linkages. Nucleic Acids Research 6(9): 3009–3023.

Baker, S.P., J. Pitha (1982) Irreversible Blockade of Beta Adrenoreceptors and Their Recovery in the Rat Heart and Lung In Vivo. The Journal of Pharmacology and Experimental Therapeutics 220(2): 247–251.

Broido, M.S., G.Zon, T.L. James (1984) Complete Assignment of the Non–Exchangeable Proton NMR Resonances of [d–(GGAATTCC)]$_2$ Using Two–Dimensional Nuclear Overhauser Effect Spectra. Biochemical and Biophysical Research Communications 119(2): 663–670.

Caruthers, M.H. et al. (1982) New Methods for Synthesizing Deoxyoligonucleotides. Genetic Engineering 4: 1–17.

Frielle, T. et al. (1987) Cloning of the cDNA for the human β1–adrenergic receptor. Proc. Natl. Acad. Sci. USA 84: 7920–7924.

Frohlich, E.D. (1986) Is the Spontaneously Hypertensive Rat A Model for Human Hypertension? Journal of Hypertension 4(Suppl 3): S15–S19.

Machida, C.A. et al. (1990) Molecular Cloning and Expression of the Rat β1–Adrenergic Receptor Gene. The Journal of Biological Chemistry 265(22): 12960–12965.

Martinez–Maldonado, M. (1991) Pathophysiology of Renovascular Hypertension. Hypertension 17(5): 707–719.

Stec, W.J. et al. (1984) Automated Solid–Phase Synthesis, Separation, and Stereochemistry of Phosphorothioate Analogues of Oligodeoxyribonucleotides. J. Am. Chem. Soc. 106: 6077–6079.

Stein, C.A. et al. (1988) Phosphorothioate and normal oligodeoxyribonucleotides with 5'–linked acridine: characterization and preliminary kinetics of cellular uptake. Gene 72: 333–341.

Gonzalez–Cabrera et al., "Selective inhibition of $\alpha_{1B}$–adrenergic receptor expression and function using a phosphorothioate antisense oligodeoxynucleotide," Mol. Pharmacol., 53(6):1034–1039, 1998.

Macrez–Leprêtre et al., "Distinct functions of $G_q$ and $G_{11}$ proteins in coupling $\alpha_1$–adrenoreceptors to $Ca^{2+}$ release and $Ca^{2+}$ entry in rat portal vein myocytes," J. Biol. Chem., 272(8):5261–5268, 1997.

Mak et al., "Localisation and expression of β–adrenoreceptor subtype mRNAs in human lung," Eur. J. Pharmacol., 302(1–3):215–221, 1996.

Møller et al., "Localization and diurnal expression of mRNA encoding the $\beta_1$–adrenoceptor in the rat pineal gland: An in situ hybridization study," Cell Tissue Res., 288(2):279–284, 1997.

Pfeffer et al., "Rhythmic variation in $\beta_1$–adrenergic receptor mRNA levels in the rat pineal gland: Circadian and developmental regulation," Eur. J. Meurosci., 10(9):2896–2904, 1998.

Primary Examiner—Robert A. Schwartzman
Assistant Examiner—Sean McGarry
Attorney, Agent, or Firm—Williams, Morgan & Amerson

[57] ABSTRACT

Oligonucleotides, and compositions thereof, are disclosed which can be administered to human and animal subjects to inhibit the expression of β1-adrenoceptor to thereby control hypertension and cardiovascular disease for prolonged periods with single doses. Methods for treating humans and animals using oligonucleotides and compositions are also disclosed.

26 Claims, 1 Drawing Sheet

ANTISENSE OLIGONUCLEOTIDES TARGETED TO β-1 ADRENOCEPTOR AND METHODS OF USE

The subject invention was made with government support under a research project supported by National Institutes of Health Grant No. HL27334. The government has certain rights in this invention.

BACKGROUND OF THE INVENTION

1. Technical Field

This invention relates to compositions and methods which are usefull for reducing hypertension in animals and humans. Specifically, it relates to antisense oligonucleotide compounds capable of binding to β-1 adrenoceptor mRNA to inhibit the expression of the β-1 adrenoceptor gene, and thereby decrease the total number of β-adrenoceptors.

2. Background Art

β-1 adrenoceptors which are distributed in the heart, kidney and blood vessels, play a role in the physiological control of blood pressure. For many years, β-1 blockers, developed as drugs, have been used for the treatment of hypertension when given daily. The mechanism of control of blood pressure is not precisely known but the value of beta-blockers in hypertension control has been underscored by the reports of the Joint National Committee on High Blood Pressure recommending beta-blockers as the first line of defense in the treatment of hypertension. Current beta-blocker drugs, however, have certain disadvantages, including: (1) they have to be taken daily, or twice a day and compliance is a problem, (2) they have central effects, leading to psychological changes that contribute to the problem of patient compliance, and (3) many of the beta-blockers now available are not specific for β-1 adrenoceptors and, therefore, have side effects.

Antisense oligonucleotides (AS-ONs) are single-stranded, short sequences of nucleotides which are complementary to specific messenger RNA (mRNA). AS-ONs bind to the mRNA and prevent the translation of the message into a cell product, such as protein receptor. Antisense oligonucleotides developed for the treatment of hypertension were targeted to angiotensin (AT), angiotensin receptor mRNA, angiotensinogen mRNA, and angiotensin converting enzyme mRNA. However, hypertension is a multifactorial disease; pharmacological approaches have shown that blockade of the renin-angiotensin system, or independent blockade of the β-1 adrenoceptors can effectively control high blood pressure.

As can be understood from the above, there remains a need for an effective β-1 adrenoreceptor blocker that is highly specific, nontoxic, produces few side effects and does not cross the blood brain barrier to produce psychological changes. Also, a beta-blocker that would last longer than a day would allow patients more flexibility in the regimen of drug dosage by taking drugs once every three to seven days.

BRIEF SUMMARY OF THE INVENTION

The subject invention concerns antisense oligonucleotides, which are complementary nucleic acid sequences that can recognize and bind to target genes or the transcribed mRNA, resulting in the arrest or inhibition of deoxyribonucleic acid (DNA) transcription or translation of the messenger ribonucleic acid (mRNA). The AS-ONs can be administered to human or animal subjects to inhibit the expression of β-1 adrenoceptors ($B_1R$) in order to control or treat hypertension and cardiovascular disease for prolonged periods with few side effects.

Another aspect of the invention concerns pharmaceutical compositions useful for inhibiting expression of $B_1R$ comprising a pharmaceutical carrier and oligonucleotides of the above kind. The pharmaceutical carrier is preferably the kind suitable for a nasal spray.

A further aspect of the invention provides a method for treating hypertension in a human comprising administering to a subject an effective amount of oligonucleotides or compositions of the above kind.

The objects of the present invention therefore include providing compounds, compositions and methods of the above kind that avoid side effects and invasive surgical procedures, are effective in small dosages and specifically target $B_1R$ mRNA. The antisense oligonucleotides of the present invention do not cross the blood brain barrier and, therefore, do not produce central effects. As AS-ONs are highly specific for a given sequence of DNA, side effects will be minimized. Further, since the antisense oligonucleotides contain nucleotide sequences which are found in the body, they are not foreign to the body.

These and still other objects and advantages of the present invention will be apparent from the description that follows.

BRIEF DESCRIPTION OF THE SEQUENCES

Figure 1:
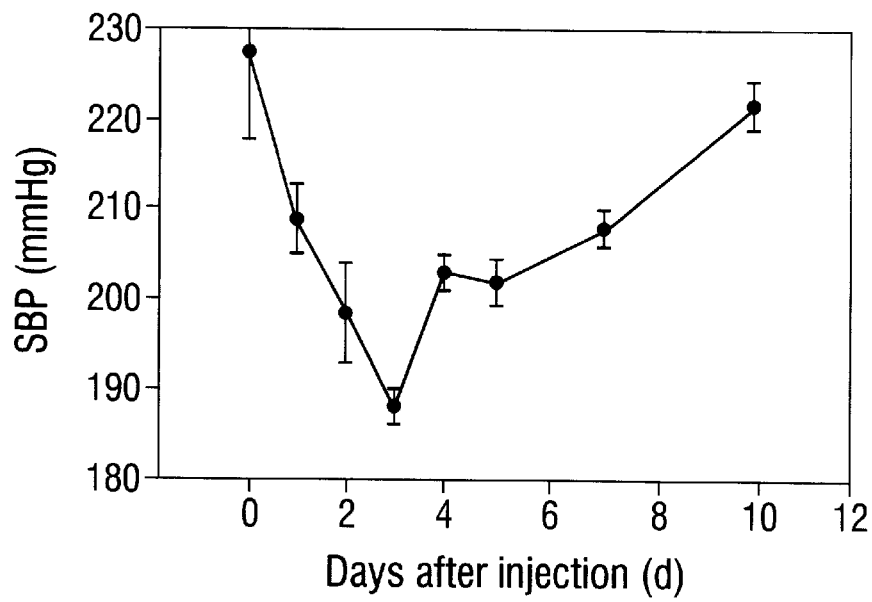
FIG. 1 shows systolic blood pressure of SHR rats after injection with 200 μg of AS-ON using tail cuff measurement (n=3; i.v. injection (tongue vein); 200 μg β1 AS #7=liposome).
Figure 2:
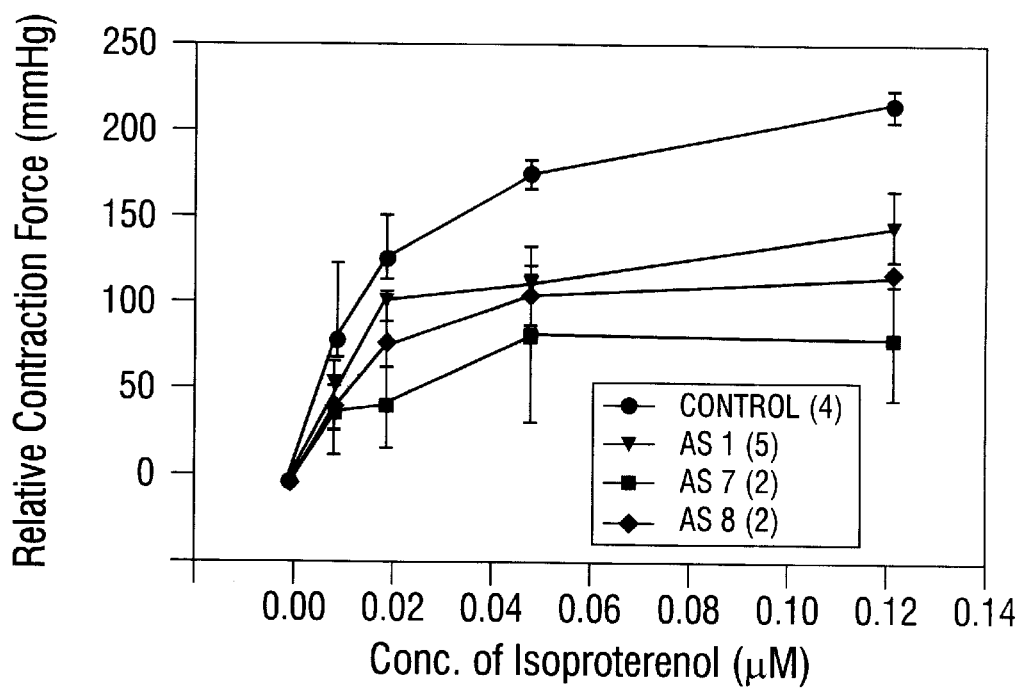
FIG. 2 shows the effects of β1 antisense on contraction force of rat heart after administration of AS-ONs control: 0.9% saline+200 μg liposome; AS: 200 μg AS in 0.9% saline+200 μg liposome; time: 24–28 hours.

SEQ ID NO. 1 is an antisense oligonucleotide which can be used according to the present invention.

SEQ ID NO. 2 is an antisense oligonucleotide which can be used according to the present invention.

SEQ ID NO. 3 is an antisense oligonucleotide which can be used according to the present invention.

DETAILED DISCLOSURE OF THE INVENTION

The subject invention concerns antisense oligonucleotides (AS-ONs), which are complementary nucleic acid sequences that can recognize and bind to target genes or the transcribed mRNA, resulting in the arrest and/or inhibition of deoxyribonucleic acid (DNA) transcription or translation of the messenger ribonucleic acid (mRNA). The AS-ONs can be administered to human or animal subjects to inhibit the expression of β-1 adrenoceptors. Thus, the AD-ONs of the present invention are useful for controlling hypertension and cardiovascular disease with few side effects for prolonged periods after single doses.

The native DNA segment coding for a β-1 adrenoceptor ($B_1R$) has, as do all such mammalian DNA strands, two strands: a sense strand and an antisense strand held together by hydrogen bonding. The messenger RNA coding for $B_1R$ has the same nucleotide sequence as the sense DNA strand except that the thymidine in DNA is replaced by uridine in DNA. Thus, synthetic antisense oligonucleotide sequences will bind to the mRNA coding for $B_1R$ and inhibit expression of the protein.

Specifically exemplified herein are oligonucleotides of the subject invention which have Formula I shown below:

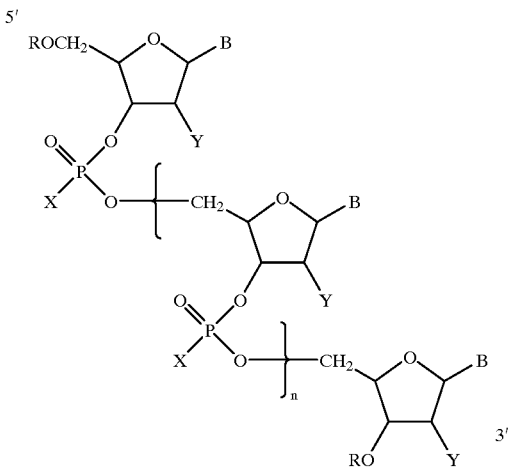

in which each X is independently selected from O, S, and $C_{1-4}$ alkyl;

each B independently is adenine, guanine, cytosine, or thymine selected such that the oligonucleotide binds to the sense DNA or mRNA strand coding for beta subtype 1 adrenoceptor ($B_1R$) to thereby inhibit the transcription or translation therefor;

each R is independently H or $C_{1-4}$ alkyl or P(O) (O)— substituted acridine;

each Y independently is H or OH;

and n is about 9 to about 25.

The oligonucleotide compound of Formula I may also be a pharmaceutically acceptable salt or hydrate thereof.

Preferably, B is selected such that the base sequence of the oligonucleotide comprises a nucleotide sequence shown in one of SEQ ID NO. 1, 2 or 3.

The oligonucleotide compounds of the invention can bind to the DNA or messenger RNA coding for $B_1R$, thereby inhibiting expression of this protein. Preferred compounds of the invention are antisense to the sense DNA sequence coding for human $B_1R$.

As used herein, the letters, A, G, C, T, and U, respectively, indicate nucleotides in which the nucleoside is adenosine (Ade), guanosine (Gua), cytidine (Cyt), thymidine (Thy), and uridine (Ura). As used herein, compounds that are antisense to $B_1R$ DNA or mRNA sense strand have a nucleoside sequence complementary to the sense strand. Table 1 shows the five possible sense strand nucleosides and their complements that would be present in an antisense strand.

TABLE 1

| Sense | Antisense |
|-------|-----------|
| Ade | Thy |
| Gua | Cyt |
| Cyt | Gua |
| Thy | Ade |
| Ura | Ade |

It will be understood by those skilled in the art that the present invention broadly includes oligonucleotide compounds which are capable of binding to the DNA or mRNA sense strand coding for $B_1R$. It will also be understood that mRNA includes not only the ribonucleotide sequences encoding a protein, but also regions including the 5'-untranslated region, the 3'-untranslated region, the 5'-cap region and the intron/exon junction regions.

The invention includes compounds which are not strictly antisense; the compounds of the invention also include those oligonucleotides that may have some bases that are not complementary to bases in the sense strand provided such compounds have sufficient binding affinity for $B_1R$ DNA or mRNA to inhibit expression. In addition, base modifications or the use of universal bases such as inosine in the oligonucleotides of the invention are contemplated within the scope of the subject invention.

The compounds of Formula I also differ from native DNA in that some or all of the phosphates in the nucleotides can be replaced by phosphorothioates (X=S) or methyphosphonates (X=CH$_3$) or other $C_{1-4}$ alkylphosphonates. The compounds of Formula I optionally may be further differentiated from native DNA by replacing one or both of the free hydroxy groups with $C_{1-4}$ alkoxy groups (R=$C_{1-4}$ alkoxy). As used herein, "$C_{1-4}$ alkyl" means a branched or unbranched hydrocarbon having 1 to 4 carbon atoms.

Compounds of the invention can also be substituted at the 3' and/or 5' ends by a substituted acridine derivative. As used herein, "substituted acridine" means any acridine derivative capable of intercalating nucleotide strands such as DNA. Preferred substituted acridines are 2-methoxy6-chloro-9-pentylaminoacridine, N-(6-chloro-2-methoxyacridinyl)-0-methoxydiisopropylaminophosphinyl-3-aminopropanol, and N-(6-chloro-2-methoxyacridinyl-0-methoxydiisopropylaminophosphinyl-5-aminopentanol. Other suitable acridine derivatives are readily apparent to persons skilled in the art having the benefit of the instant disclosure. Additionally, as used herein "P(O) (O)-substituted acridine" means a phosphate covalently linked to a substituted acridine.

The compounds of Formula I can have from about 9 to 25 nucleotides. As used herein, the term "nucleotides" includes those compounds in which the phosphate moiety is replaced by phosphorothioate or alkylphosphonate and the nucleotides may be substituted by substituted acridines. In a preferred embodiment, the compounds have from about 9 to 18 nucleotides. Most preferred are compounds having about 15 nucleotides. Compounds having fewer than 9 nucleotides are less desirable because they generally have less specificity, and compounds having greater than 25 nucleotides are generally less desirable because their physical size and charge will attenuate the crossing of the lipophilic cell membrane. Thus, they are less likely to enter cells.

Although Formula 1 compounds that are completely antisense to human $B_1R$ mRNA are preferred, the compounds of the present invention also include nucleotide compounds which lack a complement for one or more nucleotides in a segment of the DNA or mRNA sense strand provided such compounds have sufficient binding affinity for $B_1R$ DNA or mRNA to inhibit $B_1R$ expression.

Compounds of the invention in which R is H are preferred. However, R can be $C_{1-4}$ alkyl provided the resulting compounds retain sufficient binding affinity for the $B_1R$-DNA or mRNA strand to inhibit expression of $B_1R$.

Compounds of the invention in which at least one X is S can be prepared by the following published procedures: W. J. Stec, et al. (1984) *J. Am. Chem. Soc.* 106:6077–6079; S. P. Adams, et al. (1983) *J. Am. Chem. Soc.* 105:661; M. H. Caruthers, et al. (1982) *Genetic Engineering* 4:1; Settlow, J. and Hollander, A. Eds; Plenum Press: New York; M. S. Broido, et al. (1984) *Biochem. BioDhvs. Res. Commun.* 106:663. The reaction scheme described in these published procedures is conducted on a solid support. The reaction scheme can involve 1H-tetrazole-catalyzed coupling of phosphoramidites to give phosphate intermediates which are reacted with sulfur in 2,6-lutidine to give phosphate compounds. Oligonucleotide compounds can be prepared by treating the phosphate compounds with thiophenoxide (1:2:2 thiophenol/triethylamine/tetra-hydrofuran, room temperature for 1 hour). The reaction sequence is repeated until an oligonucleotide compound of the desired length has been prepared. The compounds are cleaved from the support by treating with ammonium hydroxide at room temperature for 1 hour and then are further deprotected by heating at about 50° C. overnight to yield the subject compounds. Compounds in which at least one X is oxygen are prepared by substituting 12-$H_2O$ for sulfur in 2,6-lutidine.

Compounds of the invention in which at least X is $CH_3$ or other $C_{1-4}$ alkyls can be prepared by the following published procedure: K. L. Aqarwal and F. Riftinia (1979) *Nucl. Acids Res.* 6:3009–3012. The reaction sequence is conducted on a solid support. The reaction procedure involves phosphorylation of the 3'-hydroxyl group of a 5 I-protected nucleoside using methylphosphonoditriazolide as the phosphorylating reagent followed by benzene sulfonyl catalyzed coupling of the methylphosphonates to yield the methyl phosphonate oligonucleotide. Methylphosphonoditriazolide is prepared in situ from equimolar quantities of methylphosphonodichloridate, triethylamine, and triazole. Benzene sulfonyl tetrazole can also be prepared in situ from pyridine, benzene sulfonic acid and triethylamine. Repeating this reaction sequence followed by cleavage from the support and deprotection yields compounds of Formula I.

Compounds of Formula I in which R is $C_{1-4}$ alkyl can be prepared by replacing the DMT-protected compounds with $C_{1-4}$ alkylethers.

Compounds of the invention in which R is P(O) (O)-substituted acridine also can be prepared by the following published procedures: U. Asseline and N. T. Thuong (1989) *Tet. Letters* 30(19):2521–2524; C. A. Stein, et al. (1988) *Gene* 72:333–341. These published procedures include synthesis of a nucleoside phosphoramidite-bearing acridine derivative which then is reacted with 2,2'-dithiodiethanol attached to a support. The elongation chain then is carried out on an automatic solid-phase DNA synthesized as described above. These published procedures also include synthesis of nucleoside phosphoramidite-bearing acridine derivatives by reacting substituted 9-(3-hydroxypropyl) amino acridines with N-ethyldusopropylamine followed by N,N-diisopropylmethylphosphonamidic chloride. Using an automated DNA synthesizer, compounds of the invention in which R is P(O) (O)-substituted acridine are prepared by an extra round of synthesis using the acridinyl phosphoramidites in acetonitrile.

The compounds of the present invention can be incorporated into convenient pharmaceutical dosage forms such as capsules, tablets, or injectable preparations. Solid or liquid pharmaceutical carriers can be employed. Solid carriers include, for example, starch, lacrose, calcium, sulfate dehydrate, terra alba, sucrose, talc, gelatine, agar, pectin, acacia, magnesium stearate, and stearic acid. Liquid carriers include, for example, syrup, peanut oil, olive oil, saline and water. Liposomal, viral vector, and protein conjugate preparations can also be used as carriers. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension. When a liquid carrier is used it will most often be a saline solution or phosphate buffered saline solution.

Pharmaceutical preparations can be made following conventional techniques of a pharmaceutical chemist involving mixing, granulating and compressing, when necessary, for tablet forms, or mixing, filling, and dissolving the ingredients, as appropriate, to give the desired oral or parenteral products.

Efficacious and non-toxic doses of the subject compounds (in a pharmaceutical dosage unit as described above) can be determined by ordinarily skilled clinicians. Typically, the dose may be selected from the range of 0.1 mg/kg to 500 mg/kg of active compound, but are preferably less than 1 mg/kg. The selected dose can be administered to a human patient orally, rectally, by injection, or continuously by infusion. Oral formulations would generally require somewhat larger dosages to overcome the effects of gastric decomposition. Intravenous or intraarterial administration would generally require minimum doses since the drug is placed directly into the systemic circulation. Dosages for nasal sprays would be about 20 mg (total) or 0.3 mg/kg. Therefore, the dose will depend on the actual route of administration.

In a preferred embodiment, antisense oligonucleotides of the invention are targeted to $B_1R$ mRNA and comprise specific sequences of about 15 nucleotides, bound together by phosphorothioated modified backbone, complementary to naturally occurring $B_1R$ mRNA. The AS-ON binds to $B_1R$ mRNA and prevents translation of the mRNA; thus, $B_1R$ protein production is reduced. The sequences are designed for both experimental use and for human use.

Exemplified antisense polynucleotide sequences of the subject invention include:
5'- CCG CGC CCA TGC CGA -3' (SEQ ID NO. 1)
5'- GGC CGA CGA CAG GTT -3' (SEQ ID NO. 2)
5'- ATG AGC AGC ACG ATG -3' (SEQ ID NO. 3)

The polynucleotide sequences coding for rat and human $B_1R$ polypeptide are disclosed in C. A. Machida, et al. (1990) *J. Biol. Chem.* 265:12960–12965; and T. Frielle, et al. (1987) *Proc. Natl. Acad. Sci. USA* 84(22):7920–7924.

Exemplified sequences were selected by initially focusing on the region of the AUG translation initiation codon. Once the sequences were chosen, a check was made against secondary structure with the OLIGO program to ensure that the designed oligo would not fold or anneal to itself. The BLAST program was then checked for specificity of the chosen sequence. The ordinarily skilled artisan, having the benefits of the teachings of the teachings of the present invention, can select other suitable antisense sequences using the OLIGO and BLAST programs in combination with the teachings of the subject invention.

The sequence of oligonucleotides given above are preferred sequences for inhibiting $B_1R$. Oligonucleotides having additional nucleotides at either end derived by the same process (using OLIGO and BLAST) are also contemplated within the scope of the invention. The preferred length of an ON is from about 9 to about 25 nucleotides; however, ONs of about 15 nucleotides in length work well and are economical to produce.

In one embodiment, the antisense compounds of the invention differ from native DNA by the modification of the phosphodiester backbone to extend the life of the antisense ON. For example, the phosphates can be replaced by phosphorothioates. The ends of the molecule can also be optimally substituted by any acridine derivatives which intercalate nucleotide strands of DNA.

Although the present invention has been described with reference to certain preferred embodiments, other variants are contemplated within the scope of the invention. For example, the present invention includes oligonucleotide compounds which lack a complement for each nucleotide in a particular segment of the sense strand DNA or mRNA, provided such compounds have sufficient binding affinity for the DNA or mRNA to inhibit expression thereof. The above methods can be modified when evaluating specific compounds for the inhibition of human $B_1R$ expression. For example, human cells such as human umbilical cord endothelial cells could be used for the cell culture. Also, the present invention is intended to include mixtures of different antisense oligonucleotide compounds, wherein each compound is capable of binding to β-adrenoceptor DNA or mRNA to inhibit expression of the molecule.

Following are examples which illustrate procedures for practicing the invention. These examples should not be construed as limiting. All percentages are by weight and all solvent mixture proportions are by volume unless otherwise noted.

EXAMPLE 1
Reduction of Blood Pressure in Animal Models

Animal experiments were carried out to test the efficacy and time of action of the β-1-adrenoceptor AS-ONs in reducing blood pressure in spontaneously hypertensive rats (SHR) and 2 Kidney-1 Clip Goldblatt hypertensive rats (2K-1C). The SHR and 2K-1C Goldblatt rats have been widely used for 30 years as models of human hypertension. In this regard, see E. Frolich, (1986) *J. Hypertension* 4(Suppl.3):515–519; and M. Martinez (1991) *Hypertension* 17(5):707–719. Tests were conducted in rats by intravenous injection of an antisense ON in a lipid carrier (DOTAP/DOPE 1:1 w/w) where DOTAP=N-[1(2,3-dioleoyloxy)propyl] N,N,N-trimethyl ammonium chloride and DOPE= dioleoyo phosphatidyle ethanolamine).

SHR rats tested were 6–8 months old, weighing 300–350 g. They were implanted with telemetry devices to continously record blood pressure from the aorta 24 hours a day for several weeks. A baseline was established in each case for approximately one week, then β1-AS-ON was injected intravenously and the effect on blood pressure and heart rate observed. All the ONs were effective in reducing hypertension. An AS-ON having a base sequence according to SEQ ID NO. 1 produced the greatest decrease in blood pressure and the longest-lasting effect. An AS-ON having a base sequence according to SEQ ID NO. 2 produced a similar drop in blood pressure, but the effect took place one day later than the AS-ON having SEQ ID NO. 1 and was of lesser duration. The AS-ON having a base sequence according to SEQ ID NO. 3 was also effective, but less so than the other two AS-ONs. Heart rate was not changed in any of the animals.

Dose response was tested using the AS-ON with the base sequence according to SEQ ID NO. 1 at different doses (200, 400, 800 µg of DNA). 800 µg decreased blood pressure by 20 mmHg for 4 days after injection and the effect lasted for 7 days. 400 µg decreased blood pressure by 15 mmHg and the effect lasted for 7 days. 200 µg produced a fluctuating reduction in blood pressure. The results were consistent from rat to rat (n=4 for each dose). Naked AS-ON without lipid carrier was tested as well. It produced a 10 mmHg drop in blood pressure and the effect lasted for 34 days. Inverted ON was used as a control, which shares the same composition and order of nucleotides as AS-ON but assumes the opposite direction of 5' and 3' termini. Inverted ON or lipids alone produced no effect.

Blood pressure of SHR was also measured by the tailcuff method (FIG. 1). β1-AS-ON produced a maximum drop (~40 mmHg) in systolic blood pressure (SBP) 72 hours after injection and the hypotensive effect continued for 8 days (as shown).

The next test was repeated injection. Two weeks after the first treatment, a second injection was given. Repeated injections showed that the blood pressure was again reduced with a second dose to the same extent. Thus, there was no loss of efficacy, and no evidence of tachyphylaxis. Further, no toxicity was noted.

Then 2K-1C rats were tested. Eight to ten days after the clipping of one renal artery in healthy sprague-dawley rats, blood pressure rose to the plateau by 40–50 mmHg and hypertension was readily established. 200 µg of AS-ON having a base sequence according to SEQ ID NO. 1 was given intravenously. It reduced blood pressure by 15–20 mmHg for 4 days. Again, inverted ON produced no effect.

In summary, the animal data show that the oligonucleotide having a base sequence according to SEQ ID NO. 1 was the most effective, antihypertensive agent. A single injection was effective for 8 days, and a repeated injection prolongs the antihypertensive effect. Heart rate was not affected. The ODM treatment was tolerated very well. There were no apparent side effects.

EXAMPLE 2
Inhibition of Expression of β1-adrenoceptors

β1-AS-ONs were tested in sprague-dawley rats for their ability to inhibit the expression of β1-adrenoceptors in the heart. Two days after intravenous injection of 200 µg of ODM, the rats were sacrificed and the P-adrenoceptors on the ventricular membrane were measured by binding assay disclosed in S. P. Baker and J. Pitha (1982) *J. Pharmacology and Experimental Therapeutics* 220(2):247–251. The data as shown below in Table 2 demonstrated that each of the oligonucleotides were effective in inhibiting β-adrenoceptor expression. Because β1 subtype comprises 80–90% of β-adrenoceptors in the heart and the AS-ONs used in this experiment were designed against β1 subtype specifically, the significant decrease (30–40%) in β-adrenoceptor was due to the inhibition of β1 expression.

TABLE 2

|  | Kd (pM) | Bmax (fmol/mg) | change in % |
|---|---|---|---|
| Control, no treatment | 55 | 42.1 |  |
| Control, inverted ON | 56 | 39.7 | −5.7% |
| AS-ON (SEQ ID NO. 1) | 34 | 27.5 | −34.6% |
| AS-ON (SEQ ID NO. 2) | 32 | 26.0 | −38.2% |
| AS-ON (SEQ ID NO. 3) | 36 | 38.9 | −31.4% |

Next, an isolated perfused heart model was employed to test the ability of β1-AS-ON to reduce the contractile force of rat heart in response to β-stimulation. Two days after intravenous injection of AS-ON, the hearts were perfused according to Langendorff and contractility was measured upon different doses of isoproterenol. All ONs shifted the dose response curve downward. Maximum contractile force was decreased by 30–50%.

These data demonstrate that the $B_1R$ antisense-ONs of the subject invention are beneficial as an antihypertensive agent. The AS-ON of the present invention can be used in the same way as current beta-blockers have been used, but have the advantage of being longer-lasting, and therefore taken less frequently, and are better for patient compliance.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An antisense oligonucleotide consisting essentially of the sequence of any one of SEQ ID NO:1 to SEQ ID NO:3, wherein said oligonucleotide specifically binds to a portion of mRNA expressed from a gene encoding a mammalian β-1 adrenoceptor, and further wherein binding of said oligonucleotide to said mRNA is effective in decreasing the translation of said mRNA in a host cell expressing said gene.

2. The antisense oligonucleotide of claim 1, wherein said oligonucleotide has no more than 1 mismatch from the mRNA sequence to which it specifically binds.

3. The antisense oligonucleotide of claim 1, consisting of the sequence of SEQ ID NO: 1.

4. The antisense oligonucleotide of claim 1, consisting of the sequence of SEQ ID NO:2.

5. The antisense oligonucleotide of claim 1, consisting of the sequence of SEQ ID NO:3.

6. The antisense oligonucleotide of claim 1, wherein at least one nucleotide phosphate of said oligonucleotide is substituted by a phophorothioate, a methylphosphonate, or a $C_{1-4}$ alkylphosphonate.

7. The antisense oligonucleotide of claim 1, wherein the 3' or 5' nucleotide of which further comprises a substituted acridine.

8. A compound comprising a salt or a hydrate of the antisense oligonucleotide of claim 1.

9. A composition comprising the antisense oligonucleotide of claim 1.

10. A composition comprising the antisense oligonucleotide of claim 8.

11. The composition of claim 9 or 10, further comprising a pharmaceutical excipient.

12. The composition of claim 11, wherein said pharmaceutical excipient is formulated for nasal delivery.

13. The composition of claim 9 or 10, further comprising a second antisense oligonucleotide, wherein said second oligonucleotide specifically binds to a portion of an mRNA encoding angiotensin, angiotensinogen, an angiotensin receptor polypeptide, a β-1 adrenoceptor polypeptide, or an angiotensin converting enzyme.

14. The composition of claim 9 or 10, further comprising an anti-hypertensive agent.

15. The composition of claim 14, further comprising a β-1 blocker.

16. A method for reducing expression of a gene encoding a mammalian β-1 adrenoceptor in a host cell, said method comprising providing to said host cell the antisense oligonucleotide of claim 1, the compound of claim 8, the composition of claim 10, or the composition of claim 9, in an amount effective to reduce expression of said gene in said cell.

17. A method for reducing the amount of mammalian β-1 adrenoceptor polypeptide produced by a host cell, said method comprising providing to said host cell the antisense oligonucleotide of claim 1, the compound of claim 8, the composition of claim 10, or the composition of claim 9, in an amount effective to reduce the amount of said polypeptide in said cell.

18. A method for decreasing hypertension in a mammal, said method comprising administering to a mammal in need thereof, the antisense oligonucleotide of claim 1, the compound of claim 8, the composition of claim 10, or the composition of claim 9, in an amount effective to decrease hypertension in said mammal.

19. A method for visualizing mammalian β-1 adrenoceptor-specific mRNA in a cell, said method comprising:

(a) labeling the antisense oligonucleotide of claim 1 with a detectable label;

(b) contacting the labeled antisense oligonucleotide with RNA in said cell such that hybridization between the oligonucleotide and the β-1 adrenoceptor-specific mRNA is effected; and (c) visualizing the detectable label in said cell.

20. A therapeutic kit, comprising the oligonucleotide of claim 1, the compound of claim 8, the composition of claim 10, or the composition of claim 9, and instructions for using said kit.

21. An oligonucleotide having the formula:

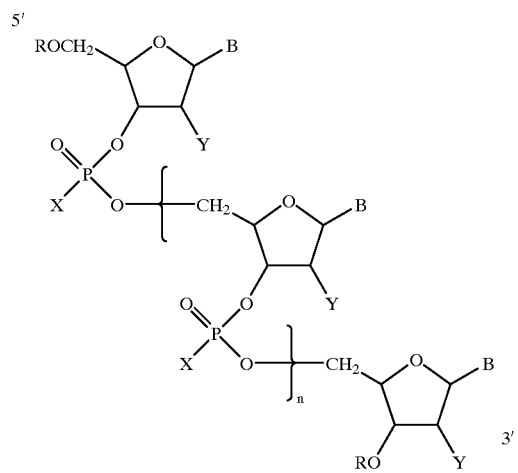

or a pharmaceutically-acceptable salt or hydrate thereof, wherein:

each X is independently selected from the group consisting of O, S and $C_{1-4}$ alkyl;

each B is independently selected from the group consisting of adenine, guanine, cytosine or thymine;

each R is independently selected from the group consisting of H, $C_{1-4}$ alkyl and P(O) (O)-substituted acridine;

each Y is independently selected from the group consisting of H and OH;

n is from about 9 to about 25; and

B is selected such that the base sequence of said oligonucleotide comprises the contiguous nucleotide sequence of SEQ ID NO: 1, SEQ ID NO:2, or SEQ ID NO:3.

22. The oligonucleotide of claim 21, wherein the base sequence of said oligonucleotide comprises the contiguous nucleotide sequence of SEQ ID NO: 1.

23. The oligonucleotide of claim 21, wherein the base sequence of said oligonucleotide comprises the contiguous nucleotide sequence of SEQ ID NO:2.

24. The oligonucleotide of claim 41, wherein the base sequence of said oligonucleotide comprises the contiguous nucleotide sequence of SEQ ID NO:3.

25. A pharmaceutical composition comprising the oligonucleotide of claim 21.

26. A method for treating hypertension in a human or animal comprising administering to a subject an amount of the oligonucleotide of claim 21 or a pharmaceutically acceptable salt or hydrate thereof sufficient to decrease translation of mammalian β-1 adrenoceptor mRNA.

* * * * *

UNITED STATES PATENT AND TRADEMARK OFFICE
CERTIFICATE OF CORRECTION

PATENT NO. : 6,087,343  
DATED : July 11, 2000  
INVENTOR(S) : M. Ian Phillips and Yuan Zhang Page 1 of 1

It is certified that error appears in the above-identified patent and that said Letters Patent is hereby corrected as shown below:

Title page,
Item [75], delete "Ian M. Phillips" and insert the following therefor: -- M. Ian Phillips, --

Column 10, claim 24,
Line 56, delete "41", and insert the following thereof: -- 21 --.

Signed and Sealed this

Fifth Day of February, 2002

Attest:

JAMES E. ROGAN  
*Attesting Officer*      *Director of the United States Patent and Trademark Office*